(12) United States Patent
Colin et al.

(10) Patent No.: US 7,491,497 B2
(45) Date of Patent: Feb. 17, 2009

(54) DEVICE FOR IMPLEMENTING AN ANALYSIS PACK, ANALYSIS PACK AND METHOD USING SAME

(75) Inventors: Bruno Colin, Marcy l'Etoile (FR); Jacques Dachaud, Besancon (FR); Marie Privat, Saint Romain en Gal (FR); Cécile Paris, Marcy l'Etoile (FR)

(73) Assignee: Biomerieux S.A., Marcy l'Etoile (FR)

( * ) Notice: Subject to any disclaimer, the term of this patent is extended or adjusted under 35 U.S.C. 154(b) by 304 days.

(21) Appl. No.: 11/251,758

(22) Filed: Oct. 18, 2005

(65) Prior Publication Data

US 2006/0078466 A1    Apr. 13, 2006

Related U.S. Application Data

(63) Continuation of application No. 10/009,848, filed as application No. PCT/FR00/01718 on Jun. 21, 2000, now abandoned.

(30) Foreign Application Priority Data

Jun. 22, 1999    (FR)    ................... 99 08117

(51) Int. Cl.
    *C12Q 1/68*    (2006.01)
    *G01N 21/00*    (2006.01)
(52) U.S. Cl. ............................. 435/6; 422/58
(58) Field of Classification Search ....................... None
    See application file for complete search history.

(56) References Cited

U.S. PATENT DOCUMENTS

| | | | |
|---|---|---|---|
| 4,390,499 A | 6/1983 | Curtis et al. | |
| 4,607,526 A | 8/1986 | Bachenheimer et al. | |
| 5,660,370 A | 8/1997 | Webster | |
| 5,726,026 A | 3/1998 | Wilding et al. | |
| 5,755,942 A | 5/1998 | Zanzucchi et al. | |
| 5,856,174 A | 1/1999 | Lipshutz et al. | |
| 5,863,502 A | 1/1999 | Southgate et al. | |
| 5,863,801 A | 1/1999 | Southgate et al. | |
| 6,074,827 A | 6/2000 | Nelson et al. | |
| 6,537,501 B1 | 3/2003 | Holl et al. | |
| 6,902,706 B1 | 6/2005 | Colin et al. | |
| 2002/0055167 A1 | 5/2002 | Pourahmadi et al. | |

FOREIGN PATENT DOCUMENTS

| | | |
|---|---|---|
| EP | 0 402 994 | 12/1990 |
| EP | 0 875 291 | 11/1998 |
| FR | 2 762 092 | 10/1998 |
| FR | 2 795 476 | 12/2000 |
| WO | WO 97/27324 | 7/1997 |
| WO | WO 98/49344 | 11/1998 |
| WO | WO 00/13795 | 3/2000 |

OTHER PUBLICATIONS

Zdeblick et al., "Thermpneumatically Actuated Microvalves and Integrated Electro-Fluidic Circuits," *Solid-State Sensor and Actuator Workshop* 251-255 (Hilton Head 1994).

*Primary Examiner*—Young J Kim
(74) *Attorney, Agent, or Firm*—Drinker Biddle & Reath LLP (57) ABSTRACT

A device for implementing a test card inside which sequential reactions and fluid transfer operations are performed under the effect of a control integrated into the card; the card includes at least two sequential reaction systems arranged in parallel, each reaction system having at least two fluid transfer systems arranged in series. A test card and the method for implementing the device and the card are also disclosed. The device contains at least one actuator per reaction line, and all the actuators are at a regular distance from one another, with the actuators preferably being equidistant. The invention is particularly applicable for the micromanipulation of fluids in biological applications.

26 Claims, 5 Drawing Sheets

DEVICE FOR IMPLEMENTING AN ANALYSIS PACK, ANALYSIS PACK AND METHOD USING SAME

This application is a continuation of U.S. application Ser. No. 10/009,848, filed Dec. 13, 2001, now abandoned which is a National Stage of International application PCT/FR00/01718, filed Jun. 21, 2000.

The invention concerns a device for implementing a test card inside which sequential reactions and fluid transfer operations are performed under the effect of control means integrated into the card. Said card includes at least two sequential reaction lines arranged in parallel, each reaction line consisting of at least two fluid transfer systems arranged in series. The invention also concerns a test card and the method for implementing the device and the card.

The invention also concerns a system for transferring flowing fluids between two devices or cards and a method for transferring flowing fluids between two devices or cards, as described above.

More precisely, the invention concerns a device or consumable (e.g. consisting of a card) inside which a reaction or at least two parallel reactions can be carried out, and which consists of an upper surface connected through an edge to a lower surface. Each of the reactions—which are physically isolated from one another—proceeds in at least one independent channel within which fluids can be made to flow by transfer means.

The background art is given in patent U.S. Pat. No. 4,585,623 which describes an apparatus for the rapid execution of chemical or immunochemical assays in a single unit. This apparatus comprises a molded plastic body (which can be miniaturized) with several reagent-containing tubes, one tube containing the sample, and another, smaller tube to receive the reaction. Since each tube is fitted with a plunger, the apparatus can be introduced into a programmable machine.

Even though it can be miniaturized, this apparatus is still relatively bulky because space has to be provided for said apparatus as well as the various connecting rods to drive the plungers. Moreover, only one reaction can be conducted with such an apparatus. If more than one reaction has to be carried out, the corresponding number of apparatuses will be needed and the time for loading each with the appropriate reagents and samples will be prolonged.

Document WO-A-97/27324 concerns a cassette for conducting parallel reactions which includes an inlet opening and an outlet opening for the transfer of one or more samples to be introduced into the cassette. Some parts of the cassette are constructed in a particular way (the Bursapak chamber, piston valve and bead valve) so that a channel is kept closed when pressure is exerted continuously from the outside.

However, this design has many disadvantages. The two main drawbacks are, on the one hand, the risk of contamination inside the cassette because it is kept at atmospheric pressure prior to its use, and on the other hand the means that actuate the cassette—the Bursapak and the piston and bead valves—which require constant presence (in terms of both time and magnitude) in order to insure that the channels concerned remain closed. Any contamination and/or the failure to keep said channels closed may result in subsequent error when the cassette is being used. Finally, keeping the channel closed in this way requires a heavy and expensive system which makes the cost of using such cassettes prohibitive.

In accordance with this invention, the proposed device solves all of the above-mentioned problems in the form of a reliable test card which is easy to manufacture and particularly easy to use, since once the valves have been actuated, they stay in the same position without the need of any additional force from outside.

To this effect, this invention concerns a device for the implementation of a test card inside which sequential reactions and fluid transfer operations are performed under the effect of control means internal to the card; said card includes at least two sequential reaction lines arranged in parallel, each line consisting of at least two fluid transfer systems arranged in series. The card contains at least one actuator per reaction line with all actuators at a regular distance from one another, preferably with all the actuators being equidistant. This device is characterized in that it includes means for displacing the card with respect to the actuators, and/or means for displacing said actuators with respect to said card.

According to a modified embodiment, the actuators act in a substantially perpendicular direction:

to the surface of said card where the actuators are acting, and/or to the directions of displacement of the card and the actuator, the one with respect to the other.

According to a modified embodiment, all the actuators are mounted on a single ramp, and each actuator can be actuated independently of the others.

According to a modified embodiment, the ramp is substantially linear and substantially perpendicular to the direction of movements of the actuators described above, and/or substantially perpendicular to the direction of movements of the card and/or of the device with respect to the card.

This invention also concerns a test card implemented by the above device, the card containing at least four control means for at least two parallel sequential reaction lines, each line having at least two control means for fluid transfer operations in series.

According to one embodiment, the configuration of all of the control means for a given reaction line is substantially linear, and the configuration of the control means for fluid transfer operations associated with one position of the ramp described above, is identical to the configuration of the control means associated with a different position of said ramp.

In the case where each reaction line includes at least one initial compartment, a receiving compartment, a fluid-carrying channel linking the two compartments, a valve acting as a control means positioned on said fluid-carrying channel (said valve controlling said channel) and with fluid flow generated by a transfer means, the arrangement of the valves on the test card is such that the fluids are allowed to flow between the initial compartment and the receiving compartment at the same time in all the reaction lines.

According to an embodiment, the valves are arranged in a substantially straight line at a regular distance from one another, preferably with all the valves being equidistant.

According to an embodiment, the axis of the straight line is perpendicular to one side of the test card.

According to an embodiment, each valve consists of at least one means which is a component that can be deformed to result in closure—directly or indirectly—of the channel, such as a flexible film covering all or part of the upper and/or lower side of the test card.

According to an embodiment, at least one of the compartments is associated with at least one buffer supply, with the buffer supply located on the opposite side of the card to the compartment with which it is associated.

According to an embodiment, each compartment which contains at least one reagent which is to be brought into contact with the sample or an aliquot of the sample, is provided with means for holding a tablet in position (consisting of an agglomerate of the reagent[s]), with said means at some distance from the bottom of said compartment.

Finally, the invention concerns a method for implementing the device and card described above, which consists in performing the following steps:

generating a pressure differential inside the card with respect to the outside, preferably a depression, introducing at least one sample to be tested into the card, sending each sample or aliquot of sample through for testing purposes, and withdrawing from or keeping in said card a part of each introduced sample.

According to a modification, testing involves performing the following operations:

denaturation of DNA and/or RNA, immobilization of DNA and/or RNA molecules on magnetic beads, amplification of said DNA and/or RNA, and screening each sample or aliquot of sample to check whether amplification has occurred.

According to a modification, the testing includes a preliminary extraction step corresponding to lysis of any cells contained in the sample.

According to a modification, the testing includes purification of the sample after extraction and before amplification.

According to a modification, testing includes analysis of the nature of the transcripts by hybridization using a biochip following amplification.

According to a modification, the card is kept in an inclined or vertical position during testing.

Preferably, the test card is displaced in a sequential manner during the various different steps and/or operations.

Still preferably, the card is displaced along two perpendicular axes in order to align the valves with the valve actuators.

The accompanying drawings are given by way of example and are not to be taken as in any way limiting with respect to the scope of the claims. They are intended to make the invention easier to understand.

Finally.

This invention as depicted in the Figures is particularly suitable for the testing of samples using the techniques of molecular biology. It concerns a card (1) which includes an edge (2) defining two planar surfaces which are parallel to one another (not labeled in the Figures).

Figure 1:
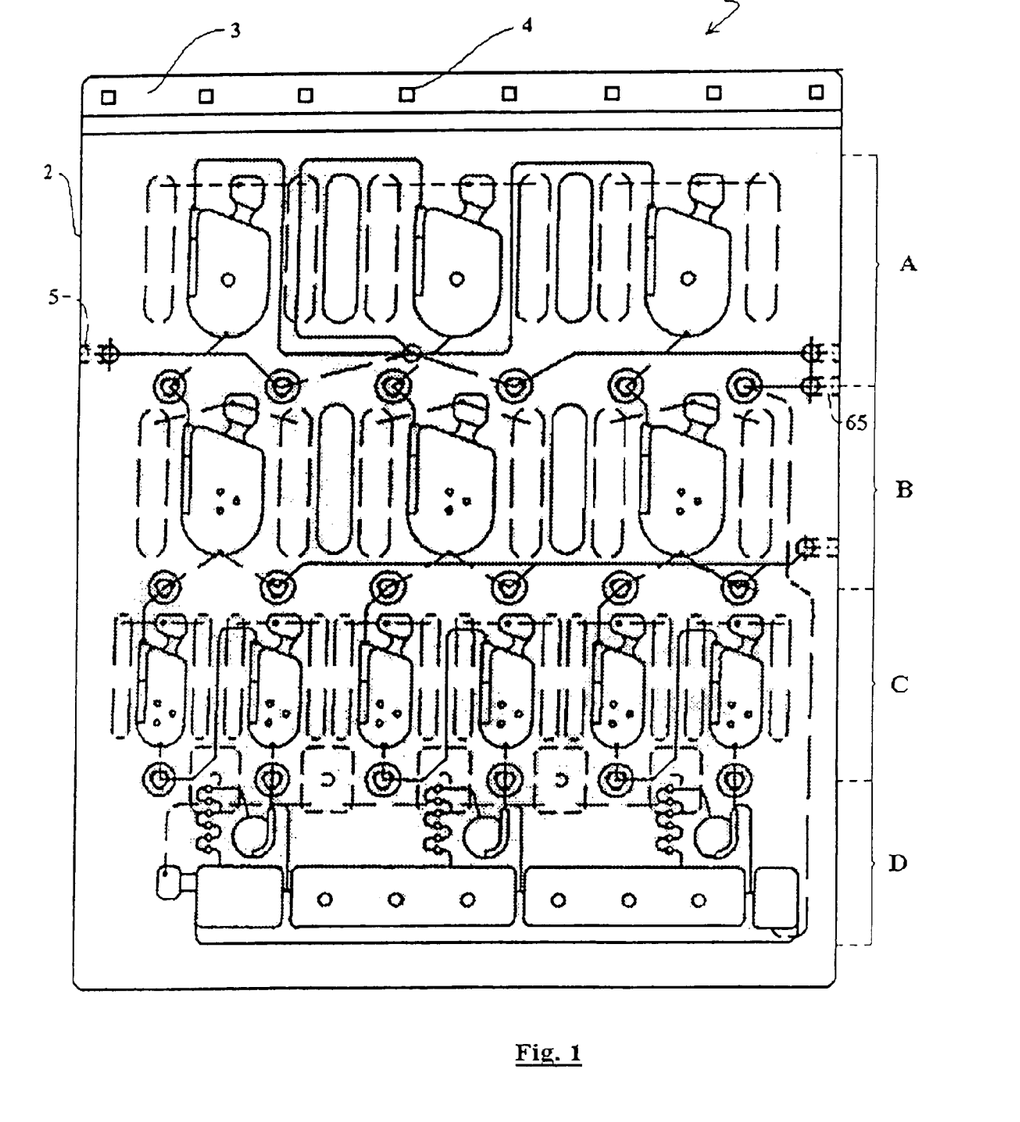
FIG. 1 shows a side view of a test card according to the invention.

In FIG. 1, it can be seen that the upper part of said card (1) consists of a strip (3) with a certain number of optical markings (4) spaced out along its length. On the sides of the card (1), i.e. along the edge (2), it can also be seen that there is a certain number of holes. On the left, there is an input opening for a test sample (5). On the right of said card (1), it can also be seen that there are three openings, one of which can be used to withdraw part of the test sample (labeled 65). In practice, part of the test sample will always be left inside the card (1) after use. Only the remaining fraction can be withdrawn for use in other tests.

More precisely, said card (1) shown in FIG. 1 is used between an initial and a final step. In the initial step, cell membranes are destroyed in order to extract intracellular DNA and/or RNA molecules, which initial step may or may not include a subsequent purification step. In the final step, nucleic acid molecules are analyzed by some detection modality after hybridization on DNA or RNA biochips.

The extraction method in the initial step could, for example, be that described in the applicant's patent applications FR97/12164 (filed on Sep. 23, 1997) and FR98/09583 (filed on Jul. 23, 1998). To enhance the efficiency of extraction, the sample could also be purified according to the applicant's patent application FR98/04878 (filed on Apr. 10, 1998).

Depending on the nature of the final step, the nucleic acids are subsequently processed by fragmentation and/or labeling so that they can be detected on a biochip. This is fully described in patent application FR98/07870 (filed on Jun. 17, 1998).

The card according to the invention makes it possible to analyze extracted DNA and/or RNA molecules using the methods referred to above. Thus, as shown in FIG. 1, the card (1) has substantially four different levels (A to D, shown on the right hand side of the Figure). Of course, these levels are in no way limiting, e.g. it would be possible to have more compartments, more valves or other elements, depending on which complementary tests are to be carried out. In this Figure, the test sample progresses through processing operations from the top towards the bottom, although this is not to be taken as limiting.

Thus, part A of the card (1) makes up the first level at which the DNA and/or RNA is denatured meaning that either the two strands of the double-stranded DNA molecule are separated, or the single RNA strand is "cleaned up", i.e. any secondary structure is abolished.

In a second step, part B of the card (1) makes up the second level where DNA and/or RNA molecules are adsorbed onto magnetic beads which can be immobilized by subjecting them to a magnetic field. The magnetic beads are not shown in the Figures. At this second level, it is also possible to perform a wash step in order to remove any material which has not been immobilized by the magnetic beads (and which is therefore unwanted). At the end of this step, the DNA and/or RNA is eluted from the magnetic beads (e.g. by a chemical process) which are then subjected to a magnetic field thereby releasing the nucleic acid molecules which can then pass on through to the third level.

At the third level (C), two distinct steps proceed in two different, adjacent compartments. In the first compartment, all the cofactors necessary for the amplification reaction are mixed together—reagents which are familiar to those skilled in the art such as oligonucleotides, primers and other reagents. The second compartment contains the enzyme which catalyzes amplification in the mixture of the target nucleic acids plus the primers, oligonucleotides, etc.

After amplification in part C, the transcripts are transferred to part D where they are screened, possibly in the presence of a marker. Depending on whether the result of the screening is positive or negative, part of the recovered biological sample right at the bottom of this card (1) may or may not be transferred via the outlet (65) to a different card or to an extension of the same card.

Moreover, it needs to be stipulated that the initial DNA extraction step, and even the purification step can be performed either in a different card and/or another apparatus, or in an extension of this same card (1). The transfer operation from one test card to another test card is covered by the applicant's patent application FR98/11383 (filed on Sep. 8, 1998)

When part of the sample leaves the outlet (65), it is recovered in order to process the DNA and/or RNA molecules so that they can be brought into contact with a biochip, as detailed in the applicant's patent application FR98/07870 (filed on Jun. 17, 1998).

FIGS. 2 to 5 show more precisely each level (A to D) one by one.

Figure 2:
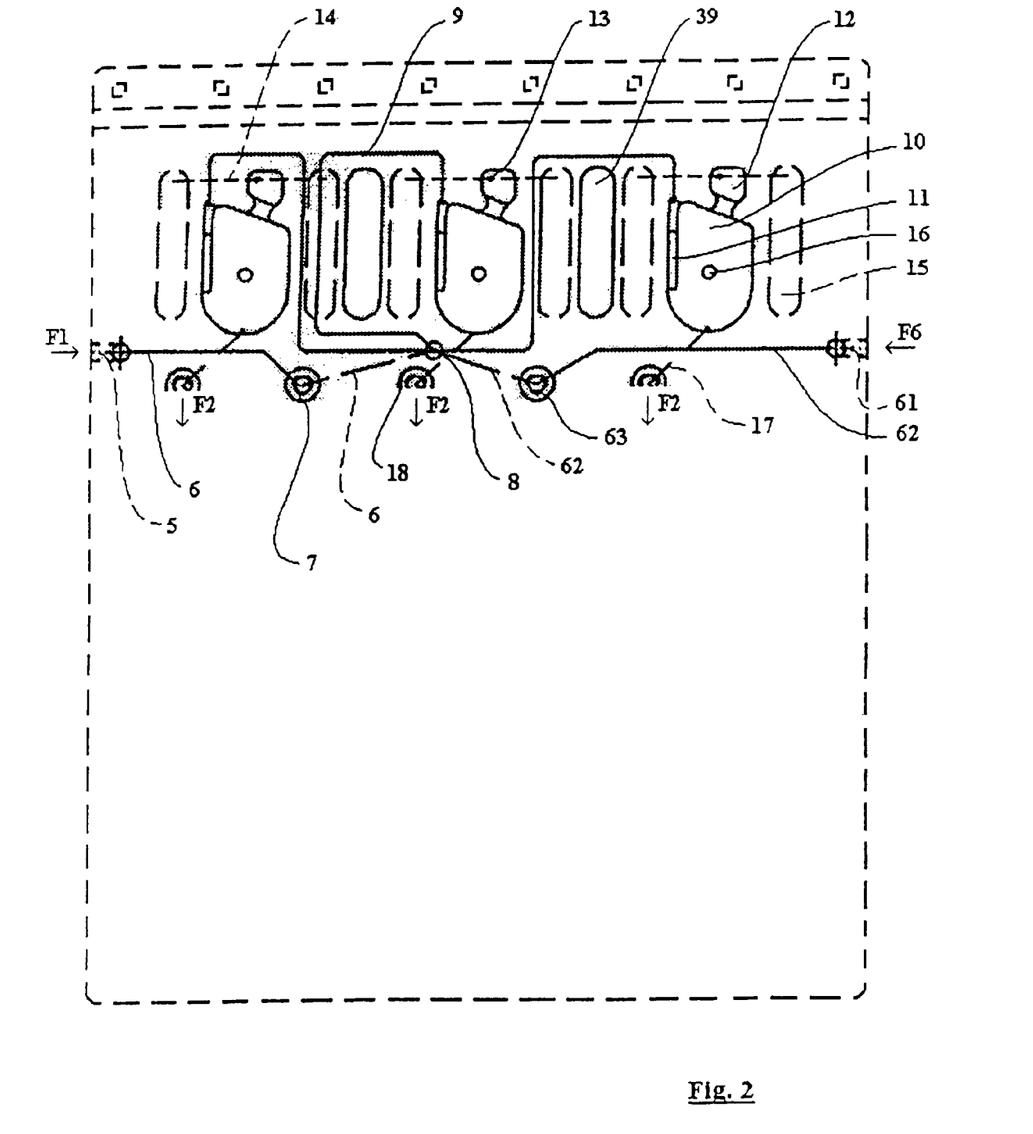
FIG. 2 shows a side view identical to that in FIG. 1 but showing the first level of the card which corresponds to the level at which DNA and RNA molecules in the extract (which may have been purified) are denatured.

Level A is clearly shown in FIG. 2. It can be seen that there is an inlet channel (6) at the test sample inlet (5) through which a liquid sample can be introduced in the direction of F1.

It should be pointed out that the structures depicted by unbroken lines on all of these Figures are located on the front of the card (1), whereas those depicted by broken lines are located on the back of the card (1). Nevertheless, it is entirely possible to imagine having holes all the way across the card (1) for various elements such as compartments; as it is the case for the thermal insulation compartments (39 and 59) which will be discussed in detail below.

The liquid sample flowing in the direction F1 will therefore reach the inside of the card when the inlet valve (7) is opened. Such a valve is described in the applicant's patent application FR98/11383 (filed on Sep. 8, 1998) already mentioned above. Beyond the valve (7), the channel (6) leads to a separator (8) which acts as a fractionater and splits the sample between all the different reaction lines. It can be seen that there are three reaction lines in the embodiment shown in these Figures. Of course, equivalent volumes of the liquid must be dispensed into each of the reaction lines. In order to achieve this, the configuration of all the primary transfer channels (9) on the first level of the card (1) located between the separator (8) and each denaturation compartment (10) on the first level, have a certain number of features which are clearly covered in patent application FR99/03035 (filed on Mar. 9, 1999) and clearly shown by way of example in FIG. 1 of this application. This is similarly true below for levels B and C (level D has instead a convergence compartment [60]).

Therefore, each primary transfer channel (9) leads to a denaturation compartment (10), the position of which means that gravity drives the liquid into it while at the same time capillary action is exploited through a means of drainage (11) which has already been described in the applicant's patent applications FR99/03034 and FR99/03035 (both submitted on Mar. 9, 1999).

Therefore, the test sample is channeled until it drops into the bottom of the compartment (10) which is associated with a system for bursting any bubbles (12) such as can always be created when a biological specimen is flowing through small-caliber channels (e.g. 6, 9, etc.) This apparatus (12) includes a communication opening (13) which connects the apparatus to two buffer supplies (15) which are located on either side of the compartment (10). A communication channel (14) links the opening (13) and the buffer supplies (15). The bubble-bursting system (12), the communication opening (13), the communication channel (14) and the buffer supply (15) are all described in patent application FR99/03035 referred to above.

The only difference lies in the position of the two buffer supplies (15) with respect to the compartment (10). It can be seen from the Figure that between two adjacent compartments (10), there are two buffer supplies (15) and also—between the two adjacent buffer supplies (15)—a first level thermal insulation compartment (39). This configuration means that between two adjacent compartments (10), there are three volumes of air to provide thermal insulation—important since the denaturation of the DNA and/or RNA is carried out at this first level and this process requires temperatures of between 90 and 100° C. The configuration prevents the over-heating of biological samples and fluids which might result not just in the desired denaturation of the nucleic acids to be analyzed, but in their destruction.

Since the volume of the compartments (10) is great, there is a stanchion (16) at the center of each to support the flexible film which covers the front of the card (1) and which defines the network of channels and compartments. This device has already been described in patent application FR99/03035 referred to above.

The card (1) is designed to work in a substantially vertical position, with the test sample introduced into each compartment (10) having to be located in the bottom of the compartment (10). At this level, there is a first level secondary transfer channel (labeled 17) which brings aliquots of the sample from the first level (A) to the second level (B) via a valve (18) which gives access to the second level (B). The liquid is delivered in the direction F2.

Figure 3:
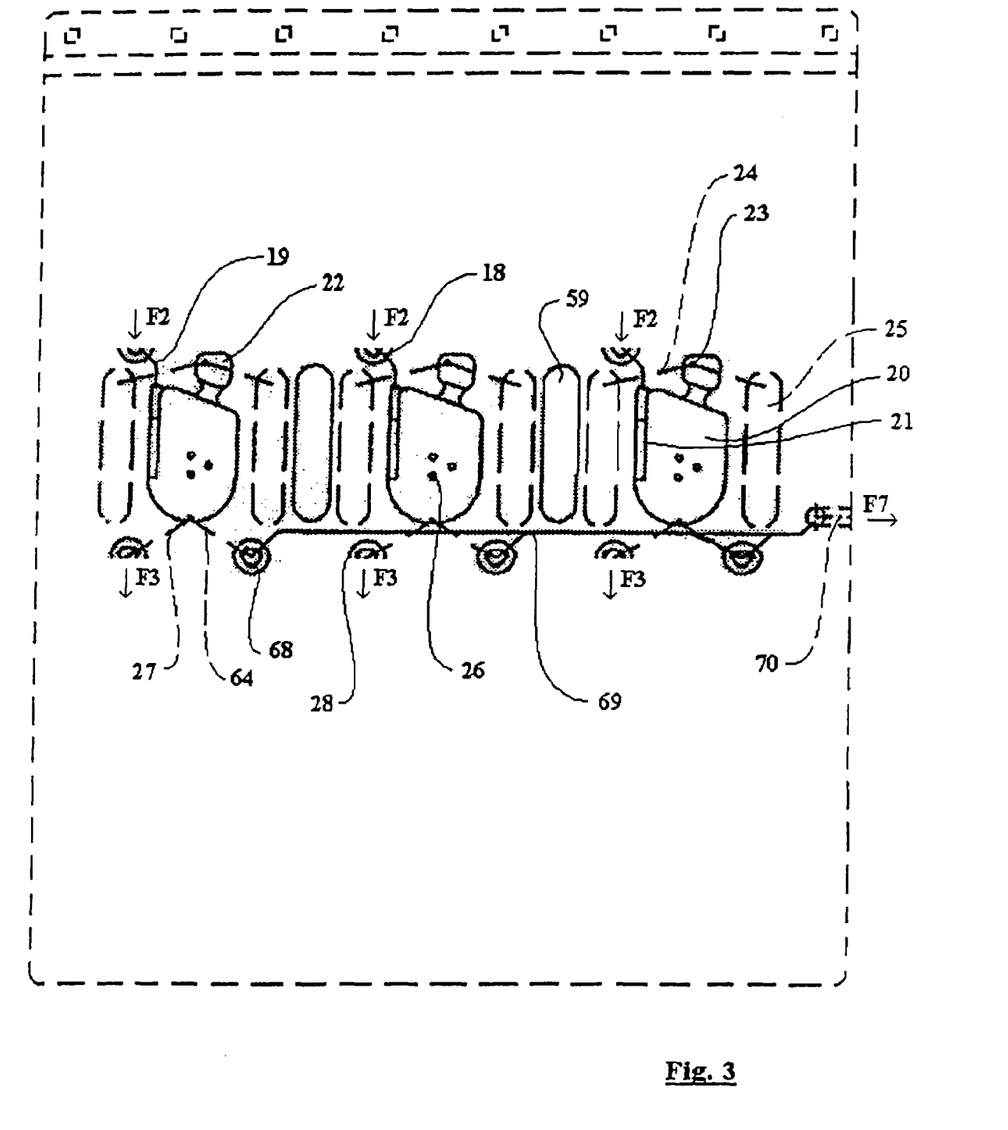
FIG. 3 shows a side view identical to that in FIG. 1 but showing the second level of the card which corresponds to the level at which DNA and RNA molecules are immobilized on magnetic beads and washed.

FIG. 3 clearly shows the second level (B) at which the valve (18) is seen again with the three aliquots of the test sample being introduced as shown by the arrows labeled F2. Beyond this valve (18), there is a second level (B) primary transfer channel (19) which carries the biological sample from the valve (18) to the immobilization compartment (20). Substantially the same features are seen as were seen at the first level, namely a means of drainage (21), a bubble-bursting system (22), and a communication opening (23) which joins the bubble-bursting system (22) to two buffer supplies (25) via a communication channel (24).

In contrast, it can be seen that, instead of a single stanchion in the middle of the compartment (20), there are three small stanchions (26) forming a triangle which is substantially isosceles in shape. This configuration is of particular worth because, at this level before the card has been used, there is a tablet held in the space between these three stanchions (26) (not shown in these Figures). This tablet is composed of an agglomerate of magnetic beads which are going to be used in the next part of the method.

The purpose of this configuration is to allow each aliquot of the test sample to flow into the compartment (20) without the magnetic bead tablet dissolving straight away and filling the underlying channels from the outset. Of course, said card (1) should be kept in a substantially vertical or inclined position—as previously and as subsequently.

In fact, the magnetic bead tablet will not dissolve until the level of the liquid reaches the first stanchion (26). This delays release of the magnetic beads which is particularly advantageous.

Also seen are two channels in the lower part through which the biological sample or any other liquid travelling through the compartment (20) can be directed. Thus, each compartment (20) is associated with one valve on the left hand side (28) and another on the right (68). Valve (28) gives a liquid coming through in the direction F3 access to the third level.

This transfer occurs via the second level secondary transfer channel (labeled 27). A second circuit is made up of an individual outlet channel (64) for the liquid—whatever it be—contained in the compartment (20). This channel ends at a second level delivery valve (68) which is itself connected to a common outlet channel (69) for the second level (B).

In fact, all of these outlet channels (64) lead to the same common channel (69) and they can all be opened or closed independently using the valves (68) on each of the channels (64). The common channel (69) leads to an outlet (70) through which whatever liquid is contained in the compartment (20) can be drained in the direction F7. The first purpose of this second circuit (comprising 64, 68, 69 and 70) is to vacuum the first and the second levels as, once performed, this vacuum makes it possible to close all the valves (68). The second purpose is to make it possible for the liquid (whatever it be, e.g. a biological sample for testing or washing medium) to flow without any input of energy. Moreover, this circuit makes it possible to perform a wash step which is implemented in the circuit comprising 64, 68, 69 and 70. Thus when the magnetic bead tablet has dissolved in the test sample, the magnetic beads will bind the nucleic acids at their surface. Such magnetic beads have for example been described in the applicant's patent applications WO-A-97/45202 (filed under priority on May 24, 1996) and PCT/FR99/00011 (filed under priority on Jan. 6, 1998).

When the nucleic acids are bound to the magnetic beads, it is possible to induce a magnetic field substantially perpendicular to the plane of the card (1) in order to immobilize the beads and their associated nucleic acids on the walls of the card (1) or the flexible film. Then a washing operation can be performed by simply introducing a liquid via the inlet opening (5) referred to above; alternatively and preferably, an inert fluid can be introduced via inlet (61) to wash out the whole of both levels (A and B), evidently with the fluid subsequently being drained via outlet (70) in the direction F7. Introducing the fluid via inlet (61) according to F6 is preferable because this network (with its inert fluid inlet channel [62] and inert fluid inlet valve [63]) is completely independent of the test sample input network and this is a safety precaution with respect to the analysis to be performed at a later stage.

It should be noted that channel (62) leads to a sample separator (8) which means that it is possible to wash out the whole of levels A and B.

Figure 4:
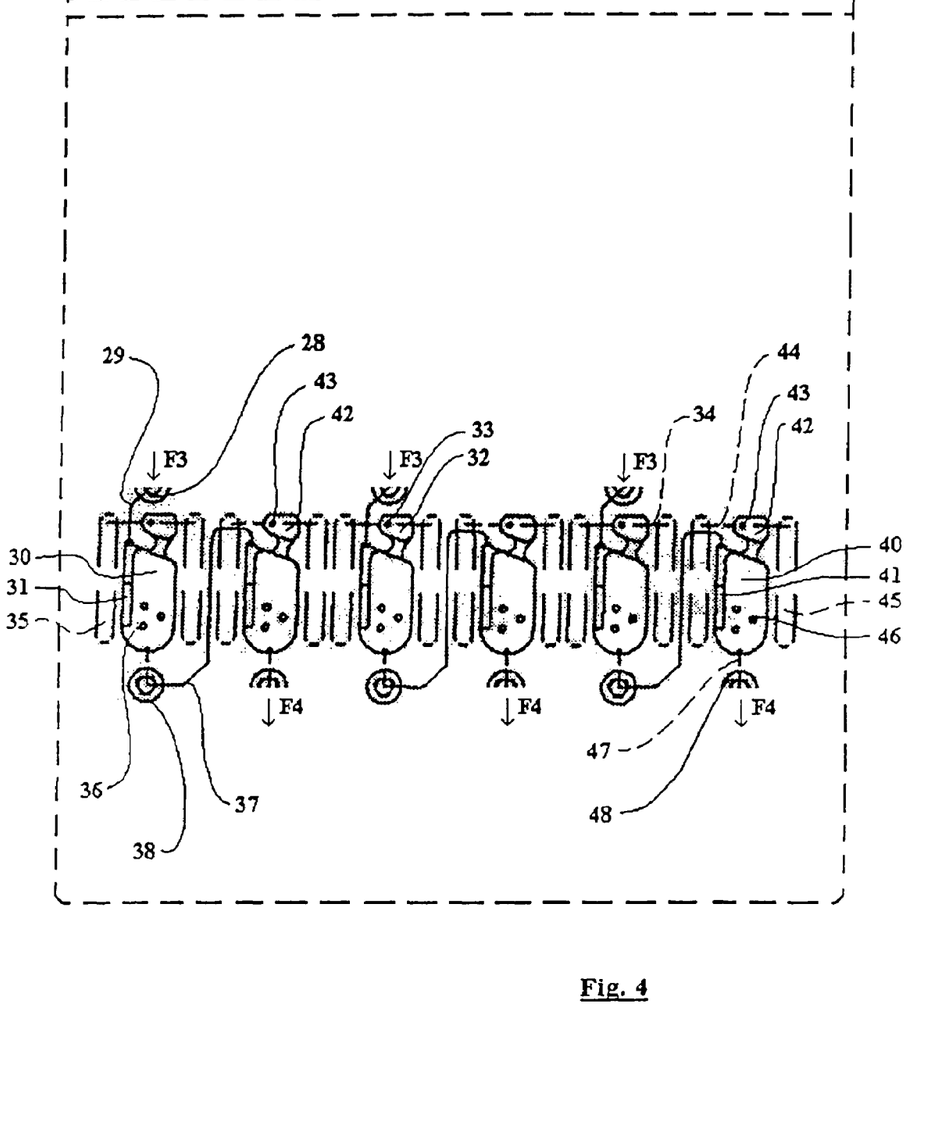
FIG. 4 shows a side view identical to that in FIG. 1 but showing the third level of the card which corresponds to the level at which said DNA and RNA molecules are amplified.

Next, the test liquid is transferred via valve (28) towards the third level (C) according to F3, as clearly shown in FIG. 4. Thus, the three aliquots of the sample pass in the direction of F3 through the open valve (28), into the third level primary transfer channel (29) and thence into the compartment (30) on the third level (C) of said card (1).

It can be seen that at this third level (C), there are twice as many compartments because each reaction line is associated with two smaller compartments arranged in series (labeled 30 and 40). How these compartments work is described below. Compartment 30 is identical to compartment 40, and both have similar features to the compartments described above (labeled 10 and 20). For example, they contain a means of drainage (31 and 41), a bubble-bursting system (32 and 42), a communication opening (33 and 43), and a communication channel (34 and 44) joining the bubble-bursting system (32 and 42) with two buffer supplies (35 and 45) for each channel (34 and 44). The configuration is similar to the above-described compartments.

Inside the compartments (30 and 40), there can be seen stanchions (36 and 46) which resemble those in level B (26), i.e. each compartment (30 or 40) contains a set of three stanchions (36 or 46) which are arranged in the geometry of an isosceles triangle and which can hold a product-containing tablet (which will be dealt with in detail below).

The pair of compartments (30 and 40) corresponding to each reaction line are joined by a third level (C) intermediate transfer channel (37). There is a valve (38) located on this channel which controls access to the second compartment (40) of third level (C). In fact and as was the case above, channel 37 joins the lower part of the first compartment (30) to the substantially higher part of the second compartment (40). In the lower part of compartment 40, there is a third level (C) secondary transfer channel (47) which leads to a valve (48) which controls access to the fourth level (D). Here, the test sample passes in the direction F4.

As mentioned above, each compartment (30 or 40) contains a product-containing tablet, the two-compartment unit (30 plus 40) being intended for the amplification of the DNA and/or RNA which was extracted, denatured and immobilized in the preceding steps. To achieve this, held between the stanchions (36) of the first compartment (30) is a tablet containing the cofactors necessary for the amplification reaction such as oligonucleotides and primers (possibly containing promoters etc.). Mixing takes place by dilution as the liquid level rises in the compartment (30) and comes into contact with the tablet as described above for the magnetic beads on level B. The same happens in the second compartment (40) where the stanchions (46) retain a different type of tablet containing the enzyme which catalyzes the amplification reaction.

It should be noted that there are no thermal insulation compartments (39 and 59) at the third level (C) as described for the first and the second levels: the reason is that the temperature at which the amplification reaction is carried out is not particularly high if a transcriptional amplification method such as TMA is used. Of course, any other amplification method could be used (e.g. PCR), in which case it might be necessary to include thermal insulation compartments like those on levels A and B described above.

Figure 5:
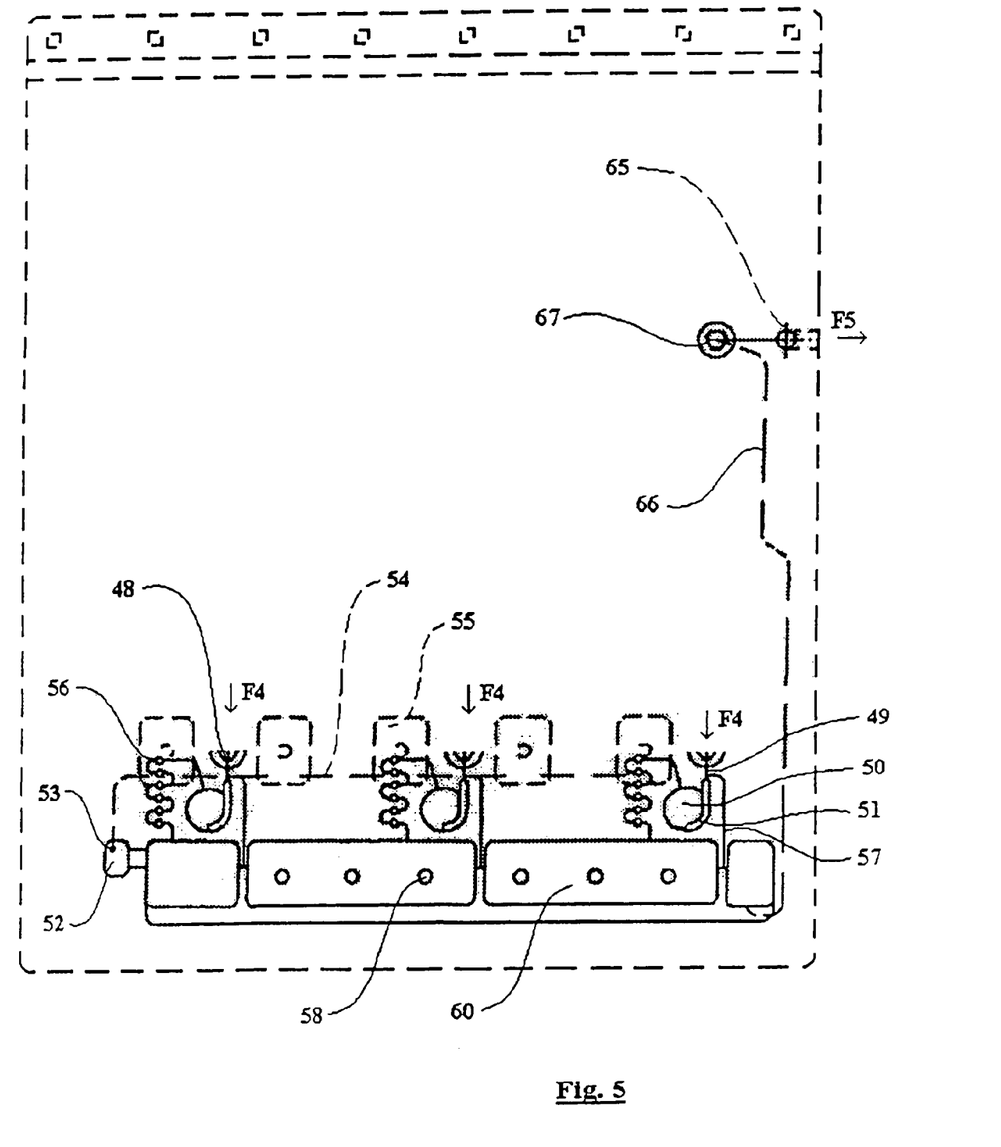
FIG. 5 shows a side view identical to that in FIG. 1 but showing the fourth level of the card which corresponds to the level at which screening is carried out to check whether amplification has occurred, and from which part of the sample is transferred on for other processes such as fragmentation, labeling, hybridization (using a biological chip referred to as biochip), and final analysis.

Level D which constitutes the fourth level is clearly depicted in FIG. 5. Again, there is a valve (48) through which the liquid arrives in the direction F4. At this level, there is a small fourth level primary transfer channel (49) which leads to a screening compartment (50) via a means of drainage (51). It can be seen that the structure of this compartment is different from that of the preceding compartments (10, 20, 30 and 40).

A fourth level (D) secondary transfer channel (57) can be seen perpendicular to the primary transfer channel (49). Since the primary transfer channel is in a substantially vertical or inclined position, the liquid which moves in the direction F4 will tend to flow from the valve (48) into the compartment (50) under the force of gravity. Therefore, at this point, no fluid will flow into the secondary transfer channel (57); the screening compartment (50) will fill up to the top where there is an isolator (56) consisting of a zig-zag channel with a certain number of broader segments which stops the liquid filling the compartment (50) from going any further (56). Thus, the isolator leads to a convergence or final compartment (60) which is located right at the bottom of the card and occupies almost the entire breadth of said card (1). When the isolator (56) is performing its function, the liquid arriving in the direction F4 will first completely fill up the compartment (50) and the rest of the sample will then flow into the secondary transfer channel (57) mentioned above. The compartment (50) is to be used for screening to monitor whether any amplification took place in the preceding step, i.e. at level C.

All the aliquots of the sample which pass through the channels (57) end up in the convergence compartment (60).

The final compartment (60), like the compartments mentioned above (10, 20, 30 and 40 but not 50) also contains a bubble-bursting system (52) which is shown on the left of this Figure. This compartment also includes an opening (53) which affords communication between the bubble-bursting system (52) and all the buffer supplies (55) which are located in the rear plane of the card whereas the isolator (56) is in this plane. The set of buffer supplies (55) is connected to the opening (53) via a communication channel (54).

The convergence compartment (60) is fairly large so it is equipped with a certain number of stanchions (58) to keep the flexible film flat (the film is not shown in the figures).

To the extreme right of the convergence compartment (60), there is another channel (66), called the outlet channel, which takes part of the test sample either to a different part of the same card (1) or to a different card (as is the case shown in the Figure). This channel (66) re-ascends towards an outlet valve (67) which communicates with an outlet (65) through which part of the test sample can be withdrawn in the direction F5.

REFERENCES

1. Card
2. Edge of the card (1)
3. Strip
4. Optical marking
5. Inlet for test sample
6. Inlet channel for test sample
7. Inlet valve for test sample
8. Sample separator
9. The first level primary transfer channel in card (1)
10. The first level or denaturation compartment
11. Means of drainage
12. Bubble-bursting system
13. Communication opening between the device (12) and at least one buffer supply (15)
14. Communication channel between the device (12) and at least one buffer supply (15)
15. Buffer supply
16. Stanchion for holding flexible film flat
17. The first level secondary transfer channel in card (1)
18. The second level access valve
19. The second level primary transfer channel in card (1)
20. The second level or immobilization compartment
21. Means of drainage
22. Bubble-bursting system
23. Communication opening between the device (22) and at least one buffer supply (25)
24. Communication channel between the device (22) and at least one buffer supply (25)
25. Buffer supply
26. Stanchion
27. The second level secondary transfer channel in card (1)
28. The third level access valve
29. The third level primary transfer channel in card (1)
30. First amplification compartment in the third level
31. Means of drainage
32. Bubble-bursting system
33. Communication opening between the device (32) and at least one buffer supply (35)
34. Communication channel between the device (32) and at least one buffer supply (35)
35. Buffer supply
36. Stanchion
37. The third level intermediate transfer channel in card (1)
38. Access valve to the second compartment (40) in the third level
39. The first level thermal insulation compartment
40. Second amplification compartment in the third level
41. Means of drainage
42. Bubble-bursting system
43. Communication opening between the device (42) and at least one buffer supply (45)
44. Communication channel between the device (42) and at least one buffer supply (45)
45. Buffer supply
46. Stanchion
47. The third level secondary transfer channel in card (1)
48. The fourth level access valve
49. The fourth level primary transfer channel
50. The fourth level screening and transferring compartment
51. Means of drainage
52. Bubble-bursting system
53. Communication opening between the device (52) and at least one buffer supply (55)
54. Communication channel between the device (52) and at least one buffer supply (55)
55. Buffer supply
56. Compartment isolator (50)
57. The fourth level secondary transfer channel in card (1)
58. Stanchion for holding flexible film flat
59. The second level thermal insulation compartment
60. Convergence or final compartment
61. Inlet for inert fluid to displace the test sample or for washing operations
62. Inert fluid inlet channel
63. Inert fluid inlet valve
64. The second level individual outlet channel in card (1)
65. Outlet for part of the test sample
66. Outlet channel for part of the test sample
67. Outlet valve in card (1)
68. The second level outlet valve in card (1)
69. The second level common outlet channel in card (1)
70. Outlet associated with common channel (69)

A. Part of the card where denaturation occurs (first level)
B. Part of the card where immobilization occurs (second level)
C. Part of the card where amplification occurs (third level)
D. Part of the card where screening and transfer occur (fourth level)
F1. Inlet for test sample
F2. Transfer of aliquots of the sample between the first and the second level
F3. Transfer of aliquots of the sample between the second and the third level
F4. Transfer of aliquots of the sample between the third and the fourth level
F5. Transfer of aliquots of the sample between the fourth level and the fifth level
F6. Inlet for inert fluid to displace the test sample or for washing operations
F7. Outlet for part of the test sample

The invention claimed is:

1. A test card inside which sequential reactions and fluid transfer operations are performed under the effect of control means integrated into the card, said card comprising: at least two sequential reaction lines arranged in parallel, each reaction line comprising at least two fluid transfer systems arranged in series, at least two valves per parallel reaction line, the valves making it possible to control fluid transfers in series within a channel from an initial level (A, B or C) to a subsequent level (B, C or D), each level corresponding to at least one processing, each valve being made up of at least a means which can be deformed by an actuator for directly or indirectly closing of said channel, wherein a distance $d_1$ between two counterpart valves belonging to different reaction lines is constant, whatever the initial level (A, B or C) from which fluid transfers which are controlled by said counterpart valves are performed, and a distance $d_2$ between the two valves belonging to the same reaction line is constant from one reaction line to another.

2. The card of claim 1, wherein each reaction line includes at least one initial compartment, one receiving compartment, a fluid-carrying channel linking the two compartments, the valve positioned on said fluid-carrying channel acting on said channel as a control means of the fluid flow generated by a transfer means, and wherein the arrangement of the valves on the test card is such that the fluids in each reaction line are allowed to flow between the initial compartment in each reaction line and the receiving compartment in each reaction line at the same time.

3. The test card of claim 2, wherein the valves are arranged along a straight line with all the valves being equidistant from one another.

4. The test card of claim 3, wherein the straight line is perpendicular to one side of the test card.

5. The test card of claim 2, wherein at least one of the compartments is associated with at least one buffer supply, and the buffer supply is located on the opposite side of the test card in relation to the compartment with which it is associated.

6. The test card of claim 1, wherein each compartment which contains at least one reagent which is to be brought into contact with the sample or an aliquot of the sample, contains a means for keeping a tablet in position, with said means at a distance from a bottom of said compartment such that said tablet is not in contact with said bottom of said compartment.

7. The test card of claim 6, wherein at the center of all or part of compartments there are a plurality of reinforcing stanchions, which make up holding means that form an isosceles triangle.

8. The test card of claim 7, wherein these stanchions are adapted to hold in place a tablet which contains particles.

9. The test card of claim 8, wherein said tablet contains magnetic particles.

10. The test card of claim 7, wherein said plurality of reinforcing stanchions comprises three stanchions.

11. The test card of claim 6, wherein said tablet comprises an agglomerate of the reagent(s).

12. The test card of claim 1, wherein said means which can be deformed by an actuator comprises a flexible film covering at least a part of the upper and/or lower part of the test card.

13. The test card of claim 1, wherein each level has a fluid inlet and a separate fluid outlet.

14. A device for implementing the test card of claim 1, which comprises at least one actuator per reaction line of said test card of claim 1 and in which all actuators are at a constant distance from one another, the device comprising means for moving the test card forward in relation to the actuators, and/or comprising means for moving said actuators forward in relation to said card, and in which each actuator can be activated independently of the others.

15. The device of claim 14, wherein the action of the actuators on the card is at a perpendicular angle: in relation to the surface of said card where the actuators operate, and/or in relation to a direction of movements of both the card and actuator.

16. The device of claim 14, wherein all the actuators are mounted on a single ramp, and the ramp is rectilinear, perpendicular to the direction of movements of the actuators, and/or perpendicular to the direction of movements of the card and/or of the device with respect to the card.

17. The device of claim 14, wherein actuators in the same ramp are equidistant.

18. A method for implementing the test card of claim 1, comprising the following steps: generating a pressure differential inside said test card with respect to the outside, introducing at least one sample to be tested into said test card, moving each sample or aliquot of sample within the test card for testing purposes, and withdrawing from or keeping in said test card a part of each introduced sample.

19. The method of claim 18, wherein the method includes the following steps: denaturing DNA and/or RNA in each sample or aliquot of sample being tested in a compartment of the test card, immobilizing DNA and/or RNA molecules in each sample or aliquot of sample being tested on magnetic beads contained within the test card, amplifying said DNA and/or RNA in at least one compartment of the test card, and screening of each sample or aliquot of sample in a compartment of the test card to check whether amplification has occurred.

20. The method of claim 19, wherein the method includes a preliminary extracting step in the test card corresponding to lysis of any cells contained in the sample.

21. The method of claim 20, wherein the method includes the step of purifying the sample in the test card after extraction and before amplification.

22. The method of claim 18, wherein the method includes the step of analyzing transcripts in the test card by hybridization using a biochip following amplification.

23. The method of claim 18, wherein the test card is used in an inclined or a vertical position during testing.

24. The method of claim 18, wherein the test card is displaced during the various different steps and/or operations in a sequential manner.

25. The method of claim 24, wherein the test card is displaced along two perpendicular axes in order to align the valves with the valve actuators.

26. The method of claim 18, wherein the step of generating a pressure differential inside said test card also generates a depression.

* * * * *